United States Patent [19]
Knifton et al.

[11] Patent Number: 4,983,565
[45] Date of Patent: Jan. 8, 1991

[54] CATALYST FOR THE PREPARATION OF LINEAR POLYETHYLENEPOLYAMINES AND METHOD OF PREPARING THE CATALYST

[75] Inventors: John F. Knifton; Wei-Yang Su, both of Austin, Tex.

[73] Assignee: Texaco Chemical Company, White Plains, N.Y.

[21] Appl. No.: 285,926

[22] Filed: Dec. 19, 1988

[51] Int. Cl.$^5$ .................. B01J 21/06; B01J 23/02; B01J 23/28; B01J 23/30
[52] U.S. Cl. .................................................. 502/242
[58] Field of Search ........................... 502/242, 309

[56] References Cited

U.S. PATENT DOCUMENTS 3,379,651  4/1968  Hargis et al. ............... 502/242 X

FOREIGN PATENT DOCUMENTS 63-130544  6/1988  Japan ................................ 502/255

Primary Examiner—W. J. Shine
Attorney, Agent, or Firm—Jack H. Park; Kenneth R. Priem; Carl G. Ries

[57] ABSTRACT

This invention is directed to novel phosphorus-free catalyst compositions based on titania pellets on which a minor amount of a tungstosilicic acid or a molybdosilicic acid is deposited. Also, the invention is directed to a process for preparing predominantly linear polyethylenepolyamines from ethylenediamine and monoethanolamine using the novel catalyst compositions.

15 Claims, No Drawings

CATALYST FOR THE PREPARATION OF LINEAR POLYETHYLENEPOLYAMINES AND METHOD OF PREPARING THE CATALYST

BACKGROUND OF THE INVENTION

1. Technical Field of the Invention

This invention relates to a process for the preparation of predominantly linear polyethylenepolyamines from ethylenediamine and monoethanolamine in the presence of unique catalyst compositions composed of titania having deposited thereon a minor amount of a tungstosilicic acid, a molybdosilicic acid on titania, a salt or a hydrate thereof.

2. Prior Art

Heretofore, polyethylenepolyamine compounds such as diethylenetriamine, triethylenetetramine and the higher homologs have been produced by the reaction of an alkyl halide such as ethylene dichloride with an amine such as ammonia or ethylenediamine at elevated temperatures and pressures. Normally, relatively high yields of predominantly non-cyclic polyethylenepolyamine compounds are obtained from this process with varying yields of heterocyclic amines. The large amounts of energy required to produce the reactants as well as the difficult separation procedures required to recover the more valuable linear polyethylenepolyamines diminish the usefulness of the ethylene dichloride process. The hydrohalide salts of ammonia and the polyethylenepolyamine products must also undergo difficult and time consuming caustic neutralization to yield the free polyethylenepolyamines.

It has heretofore been known that phosphates can be used to catalyze reactions to produce predominantly heterocyclic rather than linear products. Thus, U.S. Pat. No. 3,297,701 teaches the use of aluminum phosphate to catalyze the reaction of ethanolamines and polyethylenepolyamines to yield cyclic compounds. U.S. Pat. No. 3,342,820 discloses the use of aluminum phosphate for the preparation of heterocyclic compounds such as triethylenediamine. As another example, U.S. Pat. No. 4,103,087 also discloses the use of aluminum phosphate catalysts for producing heterocyclic product compounds.

More recently, investigators have found that more linear products can also be obtained in a catalyst conversion. Johnson et al. U.S. Pat. Nos. 4,463,193 and 4,578,517 are directed to the reaction of an alkanolamine with an alkyleneamine and ammonia in the presence of a catalytically effective amount of a group IIIB metal acid phosphate to give primarily noncyclic polyalkylene polyamine products. Thus, in Table 4 of U.S. Pat. No. 4,463,193, Johnson et al. disclose the reaction of monoethanolamine with ethylenediamine and ammonia using catalysts such as lanthanum acid phosphate and praseodynium acid phosphate at conversions of about 11 to 43% of monoethanolamine to give a noncyclic selectivity of about 67% to 92%. In Ford et al. U.S. Pat. No. 4,503,253, phosphoric acid incorporated onto an inert support (silica) was used as a catalyst and in Table 1 of the patent, use of this type of catalyst was shown to provide monoethanolamine conversions of 34% to 68% with a selectivity to noncyclics of 62% to 86%.

European patent application No. 0,073,520 dated Aug. 31, 1982 for Ford and Johnson discloses that the reaction of monoethanolamine with ethylenediamine and ammonia can be catalyzed with acidic metal phosphates, phosphoric or phosphorous acid or their anhydrides and alkyl or aryl esters (e.g., boron phosphate, ferric phosphate, aluminum phosphate, etc.). U.S. Pat. No. 4,314,083 discloses the reaction of ethylenediamine with monoethanolamine to prepare noncyclic polyalkylenepolyamines using, as a catalyst, a salt of a nitrogen or sulfur-containing compound.

In inventions originating in our laboratories, Brennan et al. in U.S. Pat. No. 4,036,881 discloses the use of phosphorus-containing catalysts to catalyze the reaction of ethylenediamine with monoethanolamine. Excellent results were obtained when the reaction was conducted in an autoclave. However, when the phosphorus compound was supported on silica or diatomaceous earth, good results were obtained only at comparatively low conversions. Brennan et al. U. S. Pat. No. 4,044,053 is also relevant in this regard. Brennan U.S. Pat. No. 4,448,997 is directed to an alumina phosphate-type catalyst composition wherein the novel feature is the method of preparing a catalyst from alumina, phosphoric acid, ammonium hydroxide and water. Excellent results were obtained using a catalyst of this nature in batch-type reactions.

More recently, Vanderpool and co-workers in a series of U.S. patents (U.S. Pat. No. 4,540,822 issued Sept. 10, 1985; U.S. Pat. Nos. 4,578,518 and 4,578,519 issued Mar. 23, 1986; 4,584,406 issued Apr. 22, 1986 and U.S. Pat. No. 4,588,842 issued May 13, 1986) have disclosed that the reaction of monoethanolamine with ethylenediamine to provide essentially noncyclic polyethylenepolyamine reaction products can be effectively promoted with catalysts composed of a minor amount of phosphorus thermally, chemically bonded to a group IVb metal oxide support such as titania or zirconia. Also, in U.S. Pat. No. 4,555,582 issued Nov. 26, 1985, Vanderpool used a zirconium silicate-supported phosphorus catalyst to promote this reaction.

Other phosphorus-containing catalysts that have been used to promote the reaction of ethylenediamine with monoethanolamine to provide essentially linear polyethylenepolyamine reaction products include those disclosed in Watts, Jr., et al. U.S. Pat. No. 4,609,761, issued Sept. 2, 1986 (catalysts comprising titania having phosphorus derived from a trialkyl phosphate or phosphite deposited thereon), and Renken U.S. Pat. No. 4,612,397, issued Sept. 16, 1986 (catalysts comprising titania having phosphorus derived from a diaminohydrogen phosphate deposited thereon).

Zimmerschied et. al. U.S. Pat. No. 2,921,081 discloses catalysts for use in the conversion of olefins that are prepared by reacting a zirconium halide with a designated class of phosphoric acids.

Rylander et. al. U.S. Pat. No. 2,824,073 is concerned with the manufacture of a titanium-phosphoric acid catalyst that can be prepared by mixing titania with triphosphoric acid to form a doughy mixture which is thereafter dried and heated.

The text, "Refractories", by F. H. Norton (McGraw-Hill Book Company, Inc., 1949) in pages 318 and 319 discloses hafnium oxide, titanium oxide and zirconium oxides as well-known refractories.

Knifton et al. U.S. Pat. No. 4,683,335 issued July 28, 1987 and entitled "Catalytic Process for the Preparation of Linear Polyethylenepolyamines with Tungstophosphoric Acid or Molybdophosphoric Acid on Titania Catalysts" discloses that titania on which minor amounts of these acids are deposited are effective in catalyzing the reaction of ethylenediamine with monoethanolamine to provide essentially linear polyethylenepolyamine reaction products. However, this reference follows the general teaching of the prior art, as outlined above, that phosphorus should be present in the catalyst.

SUMMARY OF THE INVENTION

Novel catalysts are disclosed that are prepared by depositing a minor amount of a tungstosilicic acid or a molybdosilicic acid on pelleted titania and which can be used effectively to catalyze the reaction of monoethanolamine with ethylenediamine to prepare reaction products consisting essentially of non-cyclic polyethylenepolyamines.

The novel catalysts of the claimed invention can be prepared by treating titania pellets in a manner to be described with a molybdosilicic acid or a tungstosilicic acid. The catalysts of the present invention do not contain phosphorus.

DETAILED DESCRIPTION

In one aspect of the invention the catalysts are used in producing essentially linear polyethylenepolyamines such as diethylenetriamine, triethylenetetramine, tetraethylenepentamine and pentaethylenehexamine by the catalytically promoted reaction of ethylenediamine with monoethanolamine.

In another aspect, the present invention is directed to a phosphorus-free catalyst composition composed of titania having deposited thereon a minor amount of a tungstosilicic acid, a molybdosilicic acid, or a hydrate or a salt thereof, such as an alkali metal, or an alkaline earth metal salt or a salt of aluminum or a group IB metal, etc.

Advantages of this new class of phosphorus-free catalyst compositions in comparison with the prior art include:

a. High diethylenetriamine/piperazine weight ratios, of >50.

b. High selectivity to diethylenetriamine (>90%).

c. A high percentage of noncyclics (>95%) in the triethylenetetramine range.

d. A high level of MEA conversion (>70%) at operating temperatures of 300° C. or higher.

These improvements are illustrated by the accompanying examples, but particularly Examples 3 to 6.

Thus, when monoethanolamine is reacted with ethylenediamine under the reaction conditions of the present invention, using the catalysts of the present invention, the fraction of the reaction product of the present invention boiling in the diethylenetriamine range is characterized by a high ratio of diethylenetriamine to piperazine and the fraction boiling in the triethylenetetramine ratio is characterized by a high concentration of non-cyclic polyethylenepolyamines.

The novel catalyst compositions catalyze the reaction of ethylenediamine with monoethanolamine at a temperature of from about 270° C. to about 320° C., preferably from about 290° C. to about 310° C. and a pressure of from about 1000 (68.9 bar gauge) to about 3000 psig. (206.8 bar gauge) and preferably from about 1500 (103.4 bar gauge) to about 2000 psig. (137.8 bar gauge). Higher or lower temperatures and pressures can be used, if desired, but less desirable results are obtained.

The ratio of ethylenediamine to monoethanolamine may range from about 1 to about 5 moles of ethylenediamine per mole of monoethanolamine.

The pelleted catalyst compositions of the present invention are preferably employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. Thus, in a continuous process, it is not necessary to drive the reaction to completion because unreacted feedstock components can be recycled to the reactor.

It is customary to use cylindrically-shaped catalyst pellets having a diameter essentially equal to the length thereof, such as diameters and lengths ranging from about 0.794 mm (1/32 inch) to about 9.525 mm (3/8 inch). It will be understood that the shape and dimensions of the pellets are not critical to the present invention and that pellets of any suitable shape and dimensions may be used as desired, by one wishing to practice the process of the present invention.

When cylindrical pellets of catalyst of the type described above are used, the weighted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

Catalyst life is an important factor in conducting a continuous reaction. For example, if a catalyst is easily poisoned, or if catalyst pellets do not have good structural properties, the economics of the process will be seriously and adversely affected.

The catalysts of the present invention are not particularly susceptible to poisoning so this normally does not present a problem. However, under the reaction conditions employed, amines of the type used and formed herein have the potential capability of leaching or otherwise adversely affecting the structural integrity of the pellets. In an extreme instance, catalyst pellets having good initial crush strength and surface hardness will be reduced to fines very rapidly when used under reaction conditions such as those employed herein.

As a consequence, the catalyst compositions of the present invention are advantageously used for a continuous process for the continuous production of essentially linear polyethylenepolyamine reaction products from monoethanolamine and ethylenediamine. Such catalyst compositions can be used for prolonged periods without the need for regeneration (e.g., 1,000 hours or more). Nevertheless, with the passage of time deactivation will tend to slowly occur. Deactivation can be measured qualitatively as the increase of temperature required to maintain an essentially constant conversion rate for the monoethanolamine and ethylenediamine.

The catalyst compositions of the present invention are prepared by depositing a minor amount of a molybdosilicic acid or a tungstosilicic acid on titania. Titania pellets can be prepared by extrusion or by compaction in conventional pelleting apparatus using, if necessary, a pelleting aid such as graphite. It is also within the scope of the present invention to deposit the molybdosilicic acid or tungstosilicic acid on titania followed by pelleting and calcination.

Any appropriate molybdosilicic acid or tungstosilicic acid, or their salts or hydrates, may be used to prepare the catalyst compositions of this invention. Suitable examples include those having the Keggin structures, $[SiM_{12}O_{40}]^{4-}$ and $[SiM_nO_{39}]^{8-}$, where M=molybdenum (Mo) or tungsten (W), as well as those having other condensation ratios such as $[Si_2Mo_{17}O_x]^{n-}$ and $[SiMo_{10}O_x]^{m-}$, where n, m and x are integers. Said heteropolymolybdates and tungstates may be in their acid form, or as their salts, such as alkali metal salts, e.g., sodium 12-molybdosilicate, $Na_4[SiMo_{12}O_{40}]$, potassium 12-tungstosilicate, as well as the alkali earth salts (e.g., magnesium salt), and the aluminum and group IB salts such as salts of copper, silver and aluminum. Both these heteropoly acids and their salts may be used as their hydrates.

The preferred molybdate is 12-molybdosilicic acid ($H_4SiMo_{12}O_{40}.XH_2O$) and the preferred tungstate is 12-tungstosilicic acid ($H_4SiW_{12}O_{40}.XH_2O$). These acids are preferably used in the form of an aqueous solution containing about 1% to about 50% of the acid. It is within the scope of the present invention to use an aqueous solution of two or more tungstosilicic acids or two or more molybdosilicic acids or a mixture of a tungstosilicic acid with a molybdosilicic acid.

As a matter of convenience, the normal practice is to use only one chemical as an acid source.

Preferably the catalyst composition is prepared by impregnating a preformed pellet. A suitable procedure to be used is to immerse titania pellets in an aqueous solution of the acid, preferably at ambient temperature (10° C. or higher). Higher temperatures of about 100° to about 150° C. can be used, if desired. This treatment should be continued, preferably with agitation, for about 0.1 to about 5 hours sufficient to permit the aqueous solution to penetrate the pores of the titania pellet. Suitably, the amount of aqueous solution of the acid that is used should be adequate to permit full immersion of the titania pellets. Larger amounts of the aqueous solution can be used, if desired, but there is no particular advantage in doing so. At the end of the immersion step, the excess aqueous solution can be evaporated from the treated pellets or the pellets can be removed from the aqueous solution and permitted to dry (e.g., in a drying oven).

Only a minor amount of tungstosilicic acid or molybdosilicic acid will be permanently deposited on the titania pellets by this procedure, such that the treated titania pellets will have only about 0.1 to about 10 wt. % of silicon deposited thereon, and normally about 1 wt. % or less (e.g., 0.1 to 1 wt. %). A small but significantly larger percentage of tungsten or molybdenum will be co-deposited on the titania, such as about 0.1 to about 30 wt. %, and normally from about 1 to about 10 wt. % of tungsten or molybdenum.

It will be understood that the silicon, tungsten or molybdenum that are present on thus-treated titania pellets are not present as elemental compounds, but rather as tungstosilicate or molybdosilicate groups that are chemically bound to the titania support. The exact nature of the bonding is not completely understood.

The pelleted catalyst compositions of the present invention should be calcined. They can be calcined prior to use or calcined in situ when used as catalysts at temperatures in excess of about 100° C. When the catalysts are to be calcined prior to use, calcination is suitably conducted for 2 to 24 hours at a temperature of above 100° C. but below the temperature at which thermal destruction of the chemical bonding occurs (e.g., 800° C.). This can be determined by routine experimentation for a particular catalyst. Temperatures above 900° C. should be avoided. A suitable calcining temperature range is normally 100° to 800° C. and, more preferably, 150° to 350° C.

Alternatively, the titania can be treated in powdered form with the aqueous acidic solution and the powder can thereafter be pelleted. If the pelleting treatment is conducted at a temperature of about 100° C. or more, thermal activation will normally have been obtained and it will not be absolutely necessary to conduct a calcining operation before use. If lower treating temperatures are used, calcining is normally a desired operation before use. The calcining operation can be conducted prior to or subsequent to the pelleting step.

In any event, in-situ calcining will occur when the pelleted compositions are used to catalyze the reaction of monoethanolamine with ethylenediamine at 270° to 320° C.

There are many compounds which can be formed from the reaction of ethylenediamine and monoethanolamine besides the preferred linear polyethylenepolyamines such as diethylenetriamine, triethylenetetramine, tetraethylenepentamine and pentaethylenehexamine. Less desirable cyclics and other compounds, such as piperazine, N-(2-aminoethyl)ethanolamine and N-(2-aminoethyl)piperazine, are also formed. The more desired linear polyethylenepolyamines can be easily recovered from the reaction product mixture by conventional methods such as distillation. Such distillation recovery methods are well known in the art.

Ammonia may also be added as a reactant in the generation of the preferred linear polyethylenepolyamines from ethylenediamine and monoethanolamine using the tungstosilicic acid and molybdosilicic acid on titania catalysts of this invention.

The following examples will further illustrate the preparation of predominantly linear polyethylenepolyamines from ethylenediamine and monoethanolamine by the use of the catalyst compositions of the present invention. They are given by way of illustration and not as limitations on the scope of the invention. Thus, it will be understood that reactants, proportions of reactants, and time, temperature and pressure of the reaction steps may be varied with much the same results achieved.

For purposes of convenience and brevity, the reactant compounds employed and the products obtained have been abbreviated in the following examples and tables. The abbreviations employed for these various compounds are:

EDA - ethylenediamine
MEA - monoethanolamine
PIP - piperazine
DETA - diethylenetriamine
TETA - triethylenetetramine
TEPA - tetraethylenepentamine
AEEA - N-(2-aminoethyl)ethanolamine
AEP - N-(2-aminoethyl)piperazine
HEP - N-(hydroxyethyl)piperazine

EXAMPLE 1 - PREPARATION OF 12-TUNGSTOSILICIC ACID-ON-TITANIA
(6298-25)

To 70 cc of high surface area (HSA) titania extrudates (1/8" extrudates, 51 $m^2$/g surface area) is added a solution of 10.0 g of 12-tungstosilicic acid in 50 ml of water. The mixture is stirred for 1-2 hours to absorb the liquid into the pores of the solid and excess liquid is then removed by slow evaporation. The white extrudates are calcined in a slow stream of nitrogen for 1 hour at 150° C. and 2 hours at 350° C.

Analysis of the extrudates (78.7 g) shows the presence of:
6.6% tungsten
0.1% silicon A repeat synthesis using twice the quantity of titania extrudates and 12-tungstosilicic acid gave a catalyst with essentially the same tungsten and silicon loadings.

EXAMPLE 2 - PREPARATION OF 12-MOLYBDOSILICIC ACID-ON-TITANIA (6298-23)

To 250 cc of the titania extrudates (1/8", 51 m$^2$/g surface area) is added a solution of 80 g of 12-molybdosilicic acid in ca. 200 ml of distilled water. The mixture is stirred for 1–2 hours to absorb the liquid into the pores of the solid, excess liquid is removed by evaporation, and the yellow extrudates are calcined in a slow stream of nitrogen for 1 hour at 150° C. and 2 hours at 350° C.

Analysis of the extrudates (194.1 g) shows the presence of:
10% molybdenum
0.3% silicon

EXAMPLE 3 - POLYETHYLENEPOLYAMINE SYNTHESIS (6308-74B)

To a 100 cc tubular, fixed bed reactor is charged 100 cc of the 12-tungstosilicic acid-on-titania catalyst of Example 1. A mixture of ethylenediamine and monoethanolamine (2:1 weight ratio) is then run through the reactor bed, in the upflow mode, at a series of amination temperatures, ranging from 270° to 310° C. Pressure within the reactor system is maintained at 1500 psi, the LHSV of the liquid feed is 1.0. The liquid effluent from the reactor, under steady state conditions is sampled and analyzed by glc. The data are summarized below.

TABLE I

| Operating Temp. (°C.) | MEA Conv. (%) | DETA/PIP Ratio | % Non-cyclics in TETA Range |
|---|---|---|---|
| 270 | 20.5 | 144.9 | a |
| 280 | 32.1 | 108.3 | a |
| 291 | 52.5 | 62.3 | 98.2 |
| 301 | 74.6 | 13.1 | 88.0 |
| 310 | 94.2 | 3.7 | 82.5 | a - Insufficient TETA to calculate this number.

EXAMPLE 4 - POLYETHYLENEPOLYAMINE SYNTHESIS (6308-85)

To the 100 cc tubular reactor of Example 3 is charged 100 cc of the 12-molybdosilicic acid-on-titania catalyst of Example 2. A 2:1 EDA/MEA mix is run through the reactor bed, in the upflow mode, at a series of amination temperatures. Pressure in the reactor is held at 1500 psi, the LHSV=1.0. The liquid effluent from the reactor under steady state conditions, is sampled and analyzed by glc. The data are summarized below:

TABLE II

| Operating Temp. (°C.) | MEA Conv. (%) | DETA/PIP Ratio | % Non-cyclics in TETA Range |
|---|---|---|---|
| 282 | 16.5 | 10.6 | 77.0 |
| 291 | 29.4 | 11.4 | 76.2 |
| 300 | 64.5 | 8.6 | 70.7 |
| 310 | 53.7 | 2.4 | 67.3 |

EXAMPLE 5 - POLYETHYLENEPOLYAMINE SYNTHESIS (6308-74)

To the 100 cc reactor system of Example 3 is charged the 12-tungstosilicic acid-on-titania catalyst of Example 1. A 2:1 EDA/MEA mix is fed to the reactor at a liquid hourly space-velocity (LHVS) of 4. The reactor temperature is staged from 290° to 310° C. The liquid effluent from the reactor, under steady state conditions, is sampled and analyzed by glc. The data are summarized below:

TABLE III

| Operating Temp. (°C.) | MEA Conv. (%) | DETA/PIP Ratio | % Non-cyclics in TETA Range | DETA Sel. (%) |
|---|---|---|---|---|
| 290 | 25.3 | 144.9 | 100 | 93.7 |
| 300 | 26.2 | 77.0 | 96.5 | 83.4 |
| 310 | 44.8 | 25.6 | 94.6 | 68.9 |

EXAMPLE 6 - POLYETHYLENEPOLYAMINE

To the 100 cc reactor of Example 3 is charged 100 cc of a 12-tungstosilicic acid-on-titania catalyst prepared by the method outlined in Example 1, but with less 12-tungstosilicic acid added to the titania support. The tungsten loading on this catalyst sample is 2.6 wt. %.

A 2:1 EDA/MEA mix is run through the reactor bed at a series of temperatures ranging from 280° to 310° C. Pressure in the reactor is 1500 psi. the LHSV=1.0. The liquid effluent from the reactor, under steady state conditions, is sampled and analyzed by glc. The data are summarized below:

TABLE IV

| Operating Temp. (°C.) | MEA Conv. (%) | DETA/PIP Ratio | % Non-cyclics in TETA Range | DETA Sel. (%) |
|---|---|---|---|---|
| 280 | 31.8 | 125.4 | 97.6 | 89.6 |
| 290 | 42.7 | 63.7 | 98.6 | 82.4 |
| 300 | 57.1 | 46.9 | 98.8 | 73.5 |
| 310 | 72.5 | 28.1 | 97.0 | 64.2 |

EXAMPLE 7 - POLYETHYLENEPOLYAMINE ATTEMPTED SYNTHESIS (6308-98)

To the 100 cc reactor of Example 3 is charged 100 cc of a 12-tungstosilicic acid-on-silica catalyst prepared by a method similar to that outlined in Example 1 but starting with a silica catalyst carrier (4 mm×4 mm pellets). The tungsten loading on the catalyst sample is 16.0 wt. %.

A 2:1 EDA/MEA mix is run through the reactor bed at a series of temperatures ranging from 270° to 320° C. Pressure in the reactor is 1500 psi, the LHSV=1.0. The liquid effluent from the reactor, under steady state conditions, is sampled and analyzed by glc.

No significant amounts of ethyleneamines products (DETA, TETA, etc.) were detected.

It is surprising that the excellent results, exemplified by Examples 3, 4, 5 and 6 were obtained with a phosphorus-free catalyst.

EXAMPLE 8 - POLYETHYLENEPOLYAMINE SYNTHESIS (6369-15)

To the 100 cc reactor of Example 3 is charged 90 cc of a 12-tungstosilicic acid-on-titania catalyst (6298-25), prepared by the method of Example 1, and having a tungsten loading of 7.2 wt. %.

A 2:1 EDA/MEA mix is run through the reactor bed at 300° C. Pressure in the reactor is 1500 psi. The LHSV = 1.0. The liquid effluent from the reactor, under steady state conditions, is collected over a 8½ day period and analyzed by glc. The total accumulate product volume is ca. five gallons.

Analysis of the crude product effluent are as follows:
MEA Conversion (%): 57%
DETA/PIP Ratio: 12.4
% Noncyclics in TETA Range: 88.7%

The crude ethyleneamine effluent, amounting to about 9,210 grams, was then fractionated in a two column distillation system in order to obtain a plurality of distillation cuts for gas chromatographic analysis. The results are set forth in the following tables. Distillation cuts 2 through 4 were obtained using the first distillation column and the remaining cuts 5 through 10, top and bottoms were obtained using the second distillation column.

The results that were obtained are reported in Tables V, VI and VII. Table V reports the area percents of the components detailed in each of the cuts and the percent of each of the cuts that was recovered.

The data from Table V was used to calculate the adjusted percentage for each of the components in each of the distillation cuts on the basis of a 100% recovery of each of the cuts.

The data in Table VI was then used to calculate the weight of the components in each of the cuts.

Note from Tables V through VII that the reactor effluent contained many unknown components but that, as shown by Table VII, water, unreacted ethylenediamine and unreacted monoethanolamine amounted to about 5,670 grams or 5670/9210 ×100=61% of the reactor effluent. The remaining 3,540 grams of reactor product was comprised of about 1,608 grams of diethylenetriamine or about 1608/3540×100=45%. The 515 grams of triethylenetetramine comprised about 515/3540×100=14% of the 3,540 grams.

When the components for triethylenetetramine (TETA) and tetraethylenepentamine (TEPA) were compared with pure TETA and pure TEPA, many unknown peaks were found between the major peaks for TETA and TEPA. The TETA range material was about 91.9% linear and about 8.1% cyclic, excluding the 14% unknown found in this range.

The residue material from the distillation had an amine value of 563 mg KOH/g of residue. Cut 9, which contained 87% of TETA range materials (including unknowns), had an amine value of 1,372 mg KOH/g.

TABLE V

| | Area Percent Gas Chromatographic Analysis | | | | | | | | | | | |
|---|---|---|---|---|---|---|---|---|---|---|---|---|
| | Cut # | | | | | | | | | | | |
| | 2 | 3 | 4 | 5 | 6 | 7 | 8 | 9 | 9A | 10 | Trap | Btms |
| | Sample # | | | | | | | | | | | |
| | 633-58820 | 633-58821 | 633-58824 | 633-59218 | 633-59411 | 633-59412 | 633-59423 | 633-59605 | 633-59607 | 633-59612 | 633-59614 | 633-59613 |
| H2O | 12.84 | 0.82 | 0.00 | 0.00 | 0.00 | 0.00 | 0.00 | 0.00 | 0.00 | 0.00 | 23.78 | 0.00 |
| EDA | 84.10 | 12.52 | 0.77 | 0.31 | 0.00 | 0.00 | 0.04 | 0.03 | 0.70 | 0.60 | 44.17 | 0.00 |
| Unk | 0.00 | 0.03 | 0.11 | 0.00 | 0.00 | 0.00 | 0.00 | 0.00 | 0.00 | 0.00 | 0.00 | 0.00 |
| MEA | 0.63 | 0.14 | 74.33 | 87.57 | 3.61 | 0.08 | 0.15 | 0.00 | 0.78 | 0.83 | 16.61 | 0.00 |
| Unk | 0.09 | 0.17 | 0.00 | 0.00 | 0.00 | 0.00 | 0.26 | 0.31 | 1.43 | 1.78 | 0.12 | 0.00 |
| PIP | 0.52 | 27.77 | 11.37 | 1.02 | 0.00 | 0.05 | 0.00 | 0.00 | 0.00 | 0.02 | 3.07 | 0.00 |
| Unk | 1.01 | 1.03 | 9.70 | 1.84 | 0.00 | 1.67 | 0.00 | 0.00 | 0.47 | 0.58 | 5.20 | 0.00 |
| DETA | 0.18 | 0.07 | 1.85 | 8.09 | 92.40 | 16.88 | 5.02 | 4.42 | 12.48 | 7.91 | 4.58 | 0.00 |
| Unk | 0.06 | 0.00 | 1.52 | 0.30 | 0.43 | 0.29 | 0.00 | 0.00 | 0.00 | 0.01 | 0.52 | 0.00 |
| AEEA | 0.00 | 0.00 | 0.00 | 0.77 | 0.03 | 2.47 | 38.71 | 1.91 | 0.12 | 0.89 | 0.10 | 0.00 |
| Unk | 0.00 | 0.00 | 0.00 | 0.00 | 0.00 | 0.00 | 0.94 | 1.89 | 13.87 | 17.96 | 0.00 | 0.00 |
| AEP | 0.00 | 0.00 | 0.24 | 0.07 | 3.28 | 35.87 | 1.34 | 0.00 | 0.78 | 1.17 | 0.25 | 0.00 |
| HEP | 0.00 | 0.00 | 0.00 | 0.00 | 0.07 | 11.60 | 0.95 | 0.11 | 0.00 | 0.05 | 0.09 | 0.00 |
| Unk | 0.00 | 0.00 | 0.00 | 0.03 | 0.07 | 30.89 | 14.53 | 1.95 | 2.03 | 2.36 | 0.41 | 0.00 |
| NTEA | 0.00 | 0.00 | 0.00 | 0.00 | 0.00 | 0.00 | 5.98 | 4.82 | 1.82 | 1.94 | 0.00 | 0.00 |
| Unk | 0.00 | 0.00 | 0.00 | 0.00 | 0.00 | 0.00 | 3.49 | 1.43 | 0.91 | 1.95 | 0.00 | 0.00 |
| TETA | 0.00 | 0.00 | 0.00 | 0.00 | 0.00 | 0.00 | 10.19 | 72.07 | 48.43 | 45.21 | 0.00 | 0.00 |
| Unk | 0.00 | 0.00 | 0.00 | 0.00 | 0.00 | 0.00 | 14.26* | 1.42 | 0.70 | 1.44 | 0.00 | 0.00 |
| DIAEP | 0.00 | 0.00 | 0.00 | 0.00 | 0.00 | 0.00 | 1.63 | 3.35 | 0.36 | 0.46 | 0.00 | 0.00 |
| Unk | 0.00 | 0.00 | 0.00 | 0.00 | 0.00 | 0.00 | 1.47 | 0.53 | 1.72 | 2.59 | 0.00 | 0.00 |
| PEEDA | 0.00 | 0.00 | 0.00 | 0.00 | 0.00 | 0.00 | 0.53 | 2.81 | 5.58 | 3.38 | 0.00 | 0.00 |
| Unk | 0.00 | 0.00 | 0.00 | 0.00 | 0.00 | 0.00 | 0.51 | 2.67 | 5.23 | 5.96 | 0.00 | 0.00 |
| AETETA | 0.00 | 0.00 | 0.00 | 0.00 | 0.00 | 0.00 | 0.00 | 0.00 | 0.38 | 0.98 | 0.00 | 0.00 |
| Unk | 0.00 | 0.00 | 0.00 | 0.00 | 0.00 | 0.00 | 0.00 | 0.23 | 0.64 | 1.43 | 0.00 | 0.00 |
| TEPA | 0.00 | 0.00 | 0.00 | 0.00 | 0.00 | 0.00 | 0.00 | 0.00 | 0.00 | 0.06 | 0.00 | 0.00 |
| Unk | 0.00 | 0.00 | 0.00 | 0.00 | 0.00 | 0.00 | 0.00 | 0.02 | 0.41 | 0.07 | 0.00 | 0.00 |
| AEPEEDA | 0.00 | 0.00 | 0.00 | 0.00 | 0.00 | 0.00 | 0.00 | 0.00 | 0.00 | 0.00 | 0.00 | 0.00 |
| Unk | 0.00 | 0.00 | 0.00 | 0.00 | 0.00 | 0.00 | 0.00 | 0.00 | 0.00 | 0.08 | 0.00 | 0.00 |
| PEDETA | 0.00 | 0.00 | 0.00 | 0.00 | 0.00 | 0.00 | 0.00 | 0.00 | 0.00 | 0.00 | 0.00 | 0.00 |
| PEHA/Hvys | 0.00 | 0.00 | 0.00 | 0.00 | 0.00 | 0.00 | 0.00 | 0.03 | 0.02 | 0.01 | 0.00 | 100.00 |
| Total | 99.42 | 42.56 | 99.89 | 100.00 | 99.90 | 99.80 | 99.98 | 100.00 | 98.83 | 99.72 | 98.90 | 100.00 |

*Large amount of HEDETA

TABLE VI

Area Percent Gas Chromatographic Analysis
Adjusted to a 100% Material Balance for each Cut

| | Cut # | | | | | | | | | | | |
|---|---|---|---|---|---|---|---|---|---|---|---|---|
| | 2 | 3 | 4 | 5 | 6 | 7 | 8 | 9 | 9A | 10 | Trap | Btms |
| | Sample # | | | | | | | | | | | |
| | 633-58820 | 633-58821 | 633-58824 | 633-59218 | 633-59411 | 633-59412 | 633-59423 | 633-59605 | 633-59607 | 633-59612 | 633-59614 | 633-59613 |
| H2O | 14.10 | 3.98 | 0.00 | 0.00 | 0.00 | 0.00 | 0.00 | 0.00 | 0.00 | 0.00 | 26.60 | 0.00 |
| EDA | 83.45 | 28.81 | 0.77 | 0.31 | 0.00 | 0.00 | 0.04 | 0.03 | 0.71 | 0.60 | 43.16 | 0.00 |
| Unk | 0.00 | 0.07 | 0.11 | 0.00 | 0.00 | 0.00 | 0.00 | 0.00 | 0.00 | 0.00 | 0.00 | 0.00 |
| MEA | 0.62 | 0.32 | 74.41 | 87.57 | 3.62 | 0.08 | 0.15 | 0.00 | 0.79 | 0.83 | 16.23 | 0.00 |
| Unk | 0.09 | 0.40 | 0.00 | 0.00 | 0.00 | 0.00 | 0.26 | 0.31 | 1.44 | 1.78 | 0.12 | 0.00 |
| PIP | 0.51 | 63.89 | 11.39 | 1.02 | 0.00 | 0.05 | 0.00 | 0.00 | 0.00 | 0.02 | 3.00 | 0.00 |
| Unk | 1.00 | 2.37 | 9.71 | 1.84 | 0.00 | 1.67 | 0.00 | 0.00 | 0.48 | 0.58 | 5.08 | 0.00 |
| DETA | 0.17 | 0.16 | 1.85 | 8.09 | 92.49 | 16.92 | 5.02 | 4.42 | 12.62 | 7.94 | 4.47 | 0.00 |
| Unk | 0.06 | 0.00 | 1.52 | 0.30 | 0.43 | 0.29 | 0.00 | 0.00 | 0.00 | 0.01 | 0.51 | 0.00 |
| AEEA | 0.00 | 0.00 | 0.00 | 0.76 | 0.03 | 2.48 | 38.72 | 1.90 | 0.12 | 0.89 | 0.10 | 0.00 |
| Unk | 0.00 | 0.00 | 0.00 | 0.00 | 0.00 | 0.00 | 0.94 | 1.89 | 14.04 | 18.01 | 0.00 | 0.00 |
| AEP | 0.00 | 0.00 | 0.24 | 0.07 | 3.29 | 35.94 | 1.34 | 0.00 | 0.79 | 1.18 | 0.25 | 0.00 |
| HEP | 0.00 | 0.00 | 0.00 | 0.00 | 0.07 | 11.62 | 0.95 | 0.11 | 0.00 | 0.05 | 0.09 | 0.00 |
| Unk | 0.00 | 0.00 | 0.00 | 0.03 | 0.07 | 30.95 | 14.53 | 1.95 | 2.05 | 2.36 | 0.40 | 0.00 |
| NTEA | 0.00 | 0.00 | 0.00 | 0.00 | 0.00 | 0.00 | 5.98 | 4.82 | 1.84 | 1.95 | 0.00 | 0.00 |
| Unk | 0.00 | 0.00 | 0.00 | 0.00 | 0.00 | 0.00 | 3.49 | 1.43 | 0.92 | 1.96 | 0.00 | 0.00 |
| TETA | 0.00 | 0.00 | 0.00 | 0.00 | 0.00 | 0.00 | 10.10 | 72.07 | 49.00 | 45.34 | 0.00 | 0.00 |
| Unk | 0.00 | 0.00 | 0.00 | 0.00 | 0.00 | 0.00 | 14.26 | 1.42 | 0.71 | 1.44 | 0.00 | 0.00 |
| DIAEP | 0.00 | 0.00 | 0.00 | 0.00 | 0.00 | 0.00 | 1.63 | 3.35 | 0.36 | 0.46 | 0.00 | 0.00 |
| Unk | 0.00 | 0.00 | 0.00 | 0.00 | 0.00 | 0.00 | 1.47 | 0.53 | 1.74 | 2.60 | 0.00 | 0.00 |
| PEEDA | 0.00 | 0.00 | 0.00 | 0.00 | 0.00 | 0.00 | 0.53 | 2.81 | 5.64 | 3.39 | 0.00 | 0.00 |
| Unk | 0.00 | 0.00 | 0.00 | 0.00 | 0.00 | 0.00 | 0.51 | 2.67 | 5.29 | 5.98 | 0.00 | 0.00 |
| AETETA | 0.00 | 0.00 | 0.00 | 0.00 | 0.00 | 0.00 | 0.00 | 0.00 | 0.39 | 0.99 | 0.00 | 0.00 |
| Unk | 0.00 | 0.00 | 0.00 | 0.00 | 0.00 | 0.00 | 0.00 | 0.23 | 0.64 | 1.44 | 0.00 | 0.00 |
| TEPA | 0.00 | 0.00 | 0.00 | 0.00 | 0.00 | 0.00 | 0.00 | 0.00 | 0.00 | 0.06 | 0.00 | 0.00 |
| Unk | 0.00 | 0.00 | 0.00 | 0.00 | 0.00 | 0.00 | 0.00 | 0.02 | 0.41 | 0.07 | 0.00 | 0.00 |
| AEPEEDA | 0.00 | 0.00 | 0.00 | 0.00 | 0.00 | 0.00 | 0.00 | 0.00 | 0.00 | 0.00 | 0.00 | 0.00 |
| Unk | 0.00 | 0.00 | 0.00 | 0.00 | 0.00 | 0.00 | 0.00 | 0.00 | 0.00 | 0.08 | 0.00 | 0.00 |
| PEDETA | 0.00 | 0.00 | 0.00 | 0.00 | 0.00 | 0.00 | 0.00 | 0.00 | 0.00 | 0.00 | 0.00 | 0.00 |
| PEHA/Hvys | 0.00 | 0.00 | 0.00 | 0.00 | 0.00 | 0.00 | 0.00 | 0.03 | 0.02 | 0.01 | 0.00 | 100.00 |
| Total | 100.00 | 100.00 | 100.00 | 100.00 | 100.00 | 100.00 | 100.00 | 100.00 | 100.00 | 100.00 | 100.00 | 100.00 |

TABLE VII

Weight of Components

| | Cut # | | | | | | | | | | | | | |
|---|---|---|---|---|---|---|---|---|---|---|---|---|---|---|
| | 2 | 3 | 4 | 5 | 6 | 7 | 8 | 9 | 9A | 10 | Trap | Btms | | |
| | Sample # | | | | | | | | | | | | | |
| | 633-58820 | 633-58821 | 633-58824 | 633-59218 | 633-59411 | 633-59412 | 633-59423 | 633-59605 | 633-59607 | 633-59612 | 633-59614 | 633-59613 | Total (g) | Yield % |
| H2O | 668.62 | 1.83 | 0.00 | 0.00 | 0.00 | 0.00 | 0.00 | 0.00 | 0.00 | 0.00 | 2.26 | 0.00 | 672.71 | 7.42 |
| EDA | 2956.98 | 13.25 | 1.76 | 2.68 | 0.00 | 0.00 | 0.12 | 0.16 | 0.48 | 1.11 | 3.67 | 0.00 | 3980.21 | 43.93 |
| Unk | 0.00 | 0.03 | 0.26 | 0.00 | 0.00 | 0.00 | 0.00 | 0.00 | 0.00 | 0.00 | 0.00 | 0.00 | 0.29 | 0.00 |
| MEA | 29.50 | 0.15 | 170.03 | 757.00 | 56.65 | 0.07 | 0.52 | 0.00 | 0.54 | 1.53 | 1.38 | 0.00 | 1017.38 | 11.23 |
| Unk | 4.19 | 0.18 | 0.00 | 0.00 | 0.00 | 0.00 | 0.88 | 1.57 | 0.98 | 3.29 | 0.01 | 0.00 | 11.10 | 0.12 |
| PIP | 24.28 | 29.39 | 26.02 | 8.84 | 0.00 | 0.04 | 0.00 | 0.00 | 0.00 | 0.04 | 0.25 | 0.00 | 88.85 | 0.98 |
| Unk | 47.28 | 1.09 | 22.18 | 15.94 | 0.00 | 1.39 | 0.00 | 0.00 | 0.32 | 1.07 | 0.43 | 0.00 | 89.72 | 0.99 |
| DETA | 8.23 | 0.07 | 4.23 | 69.96 | 1448.90 | 14.12 | 17.08 | 22.28 | 8.58 | 14.64 | 0.38 | 0.00 | 1608.49 | 17.75 |
| Unk | 2.92 | 0.00 | 3.47 | 2.59 | 6.76 | 0.24 | 0.00 | 0.00 | 0.00 | 0.02 | 0.04 | 0.00 | 16.05 | 0.18 |
| AEEA | 0.00 | 0.00 | 0.00 | 6.61 | 0.49 | 2.07 | 131.84 | 9.61 | 0.08 | 1.64 | 0.01 | 0.00 | 152.35 | 1.68 |
| Unk | 0.00 | 0.00 | 0.00 | 0.00 | 0.00 | 0.00 | 3.21 | 9.52 | 9.55 | 33.23 | 0.00 | 0.00 | 55.51 | 0.61 |
| AEP | 0.00 | 0.00 | 0.55 | 0.61 | 51.49 | 30.01 | 4.57 | 0.00 | 0.54 | 2.17 | 0.02 | 0.00 | 89.96 | 0.99 |
| HEP | 0.00 | 0.00 | 0.00 | 0.00 | 1.14 | 9.71 | 3.23 | 0.56 | 0.00 | 0.09 | 0.01 | 0.00 | 14.73 | 0.16 |
| Unk | 0.00 | 0.00 | 0.00 | 0.27 | 1.07 | 25.84 | 49.48 | 9.83 | 1.39 | 4.36 | 0.03 | 0.00 | 92.27 | 1.02 |
| NTEA | 0.00 | 0.00 | 0.00 | 0.00 | 0.00 | 0.00 | 20.35 | 24.34 | 1.25 | 3.59 | 0.00 | 0.00 | 49.52 | 0.55 |
| Unk | 0.00 | 0.00 | 0.00 | 0.00 | 0.00 | 0.00 | 11.89 | 7.21 | 0.63 | 3.61 | 0.00 | 0.00 | 23.34 | 0.26 |
| TETA | 0.00 | 0.00 | 0.00 | 0.00 | 0.00 | 0.00 | 34.69 | 363.59 | 33.32 | 83.64 | 0.00 | 0.00 | 515.25 | 5.69 |
| Unk | 0.00 | 0.00 | 0.00 | 0.00 | 0.00 | 0.00 | 48.57 | 7.18 | 0.48 | 2.66 | 0.00 | 0.00 | 58.90 | 0.65 |
| DIAEP | 0.00 | 0.00 | 0.00 | 0.00 | 0.00 | 0.00 | 5.54 | 16.92 | 0.25 | 0.85 | 0.00 | 0.00 | 23.57 | 0.26 |
| Unk | 0.00 | 0.00 | 0.00 | 0.00 | 0.00 | 0.00 | 5.01 | 2.68 | 1.18 | 4.79 | 0.00 | 0.00 | 13.67 | 0.15 |
| PEEDA | 0.00 | 0.00 | 0.00 | 0.00 | 0.00 | 0.00 | 1.79 | 14.17 | 3.84 | 6.25 | 0.00 | 0.00 | 26.06 | 0.29 |
| Unk | 0.00 | 0.00 | 0.00 | 0.00 | 0.00 | 0.00 | 1.72 | 13.45 | 3.60 | 11.03 | 0.00 | 0.00 | 29.80 | 0.33 |
| AETETA | 0.00 | 0.00 | 0.00 | 0.00 | 0.00 | 0.00 | 0.00 | 0.00 | 0.26 | 1.82 | 0.00 | 0.00 | 2.08 | 0.02 |
| Unk | 0.00 | 0.00 | 0.00 | 0.00 | 0.00 | 0.00 | 0.00 | 1.17 | 0.44 | 2.65 | 0.00 | 0.00 | 4.26 | 0.05 |
| TEPA | 0.00 | 0.00 | 0.00 | 0.00 | 0.00 | 0.00 | 0.00 | 0.00 | 0.00 | 0.11 | 0.00 | 0.00 | 0.11 | 0.00 |
| Unk | 0.00 | 0.00 | 0.00 | 0.00 | 0.00 | 0.00 | 0.00 | 0.12 | 0.28 | 0.14 | 0.00 | 0.00 | 0.54 | 0.01 |
| AEPEEDA | 0.00 | 0.00 | 0.00 | 0.00 | 0.00 | 0.00 | 0.00 | 0.00 | 0.00 | 0.00 | 0.00 | 0.00 | 0.00 | 0.00 |
| Unk | 0.00 | 0.00 | 0.00 | 0.00 | 0.00 | 0.00 | 0.00 | 0.00 | 0.00 | 0.14 | 0.00 | 0.00 | 0.14 | 0.00 |
| PEDETA | 0.00 | 0.00 | 0.00 | 0.00 | 0.00 | 0.00 | 0.00 | 0.00 | 0.00 | 0.00 | 0.00 | 0.00 | 0.00 | 0.00 |
| PEHA/Hvys | 0.00 | 0.00 | 0.00 | 0.00 | 0.00 | 0.00 | 0.00 | 0.13 | 0.01 | 0.02 | 0.00 | 424.00 | 424.16 | 4.68 |

TABLE VII-continued

| | | | | | Weight of Components Cut # | | | | | | | | | |
|---|---|---|---|---|---|---|---|---|---|---|---|---|---|---|
| | 2 | 3 | 4 | 5 | 6 | 7 | 8 | 9 | 9A | 10 | Trap | Btms | | |
| | | | | | | | Sample # | | | | | | | |
| | 633-58820 | 633-58821 | 633-58824 | 633-59218 | 633-59411 | 633-59412 | 633-59423 | 633-59605 | 633-59607 | 633-59612 | 633-59614 | 633-59613 | Total (g) | Yield % |
| Total | 4742.00 | 46.00 | 228.50 | 864.50 | 1566.50 | 83.50 | 340.50 | 504.50 | 68.00 | 184.50 | 8.50 | 424.00 | 9061.00 | 100.00 |

The foregoing examples have been given by way of illustrating only and are not intended as limitations on the scope of this invention, as defined by the appended claims.

What is claimed is:

1. As a new composition of matter, a catalytically active phosphorous-free pelleted composition, said composition having been prepared by the method which consists essentially of impregnating titania pellets with an aqueous solution consisting essentially of:
   a. an acid or a hydrate thereof selected from the group consisting of tungstosilicic acid and molybdosilicic acid, and their alkali metal, alkaline earth metal, aluminum and Group IB metal salts,
   b. thereafter drying and calcining said thus-treated titania pellets to thereby provide a catalyst composition consisting essentially of titania pellets having from about 0.1 to about 10 wt. % of silicon and about 0.1 to about 30 wt. % of tungsten or molybdenum deposited on the said impregnated titania pellets.

2. A composition as in claim 1 wherein a minor amount of a tungstosilicic acid is deposited on the titania pellets.

3. A composition as in claim, 2 wherein the tungstosilicic acid is 12-tungstosilicic acid.

4. A composition as in claim 1 wherein a minor amount of a molybdosilicic acid is deposited on the titania pellets.

5. A composition as in claim 4 wherein the molybdosilicic acid is 12-molybdosilicic acid.

6. As a new composition of matter, a phosphorous-free catalytically active pelleted composition:
   a. said composition having been prepared by a process consisting essentially of immersing titania pellets for about 0.1 to 5 hours at a temperature of about 10 to about 150° C. in about a 0.1 to about 50 wt. % aqueous solution consisting essentially of an acid or a hydrate thereof selected from the group consisting of tungstosilicic acid and molybdosilicic acid, and their alkali metal, alkaline earth metal, aluminum and Group IB metal salts, and
   b. thereafter drying and calcining said thus-impregnated titania pellets at a temperature of from about 200° to about 800° C. for about 2 to about 24 hours to thereby provide a catalyst composition consisting essentially of titania pellets having from about 0.1 to about 10 wt. % of silicon and about 0.1 to about 30 wt. % of tungsten or molybdenum deposited on the said impregnated pellets.

7. A composition as in claim 6 wherein a minor amount of a tungstosilicic acid is deposited on the titania pellets.

8. A composition as in claim 7 wherein the tungstosilicic acid is 12-tungstosilicic acid.

9. A composition as in claim 6 wherein a minor amount of a molybdosilicic acid is deposited on the titania pellets.

10. A composition as in claim 9 wherein the molybdosilicic acid is 12-molybdosilicic acid.

11. A method of preparing a phosphorous-free catalytically active pelleted composition which consists essentially of:
    a. immersing titania pellets for about 0.1 to 5 hours at a temperature of about 10° to about 150° C. in about a 0.1 to about 50 wt. % aqueous solution of an acid or a hydrate thereof selected from the group consisting of tungstosilicic acid and molybdosilicic acid, and
    b. thereafter drying and calcining said thus-impregnated titania pellets at a temperature of from about 150° to about 350° C. for about 2 to 24 hours to thereby provide a catalyst composition consisting essentially of titania pellets having from about 0.1 to about 10 wt. % of silicon and from about 0.1 to about 30 wt. % of tungsten or molybdenum deposited on the said impregnated titania pellets.

12. A method as in claim 11 wherein a minor amount of a tungstosilicic acid is deposited on the titania pellets.

13. A method as in claim 12 wherein the tungstosilicic acid is 12-tungstosilicic acid.

14. A method as in claim 11 wherein a minor amount of a molybdosilicic acid is deposited on the titania pellets.

15. A method as in claim 14 wherein the molybdosilicic acid is 12-molybdosilicic acid.

* * * * *